United States Patent
Raulerson et al.

(10) Patent No.: US 7,064,330 B2
(45) Date of Patent: Jun. 20, 2006

(54) INFRARED DEFECT DETECTION VIA BROAD-BAND ACOUSTICS

(75) Inventors: David Raulerson, Palm Beach Gardens, FL (US); Zhong Ouyang, Glastonbury, CT (US); Kevin D. Smith, Glastonbury, CT (US)

(73) Assignee: United Technologies Corporation, Hartford, CT (US)

( * ) Notice: Subject to any disclaimer, the term of this patent is extended or adjusted under 35 U.S.C. 154(b) by 342 days.

(21) Appl. No.: 10/426,399

(22) Filed: Apr. 30, 2003

(65) Prior Publication Data

US 2004/0217289 A1 Nov. 4, 2004

(51) Int. Cl.
*G01J 5/02* (2006.01)

(52) U.S. Cl. ............... 250/341.6; 250/334; 250/338.1; 250/338.3

(58) Field of Classification Search ........... 250/341.6, 250/334, 338.1, 338.3
See application file for complete search history.

(56) References Cited

U.S. PATENT DOCUMENTS

| 4,874,251 | A  | * | 10/1989 | Thomas et al. ............... 374/45 |
| 6,236,049 | B1 |   | 5/2001  | Thomas et al. |
| 6,399,948 | B1 | * | 6/2002  | Thomas et al. .......... 250/341.6 |
| 6,437,334 | B1 | * | 8/2002  | Thomas et al. .......... 250/341.6 |
| 6,781,127 | B1 | * | 8/2004  | Wolff et al. .................. 250/332 |
| 6,998,616 | B1 | * | 2/2006  | Favro et al. ............. 250/341.6 |
| 2002/0172410 | A1 | | 11/2002 | Shepard |
| 2003/0010124 | A1 | | 1/2003 | Bates |
| 2004/0089812 | A1 | * | 5/2004 | Favro et al. ............. 250/341.6 |
| 2004/0119019 | A1 | | 6/2004 | Thompson et al. |
| 2004/0245469 | A1 | * | 12/2004 | Favro et al. ............. 250/341.6 |
| 2005/0151083 | A1 | * | 7/2005 | Favro et al. ............. 250/341.6 |

FOREIGN PATENT DOCUMENTS

DE 19838858 4/1999
JP 05045314 A * 2/1993

OTHER PUBLICATIONS

L.D. Favro et al., Review of Scientific Instruments, American Institute of Physics, Jun. 2000, pp. 2418-2421, vol. 7, No. 6.

Thomas Zweschper, Alexander Dillenz and Gerd Busse, "NDE of adhesive joints and riveted structures with lock-in thermography methods", Proceedings of SPIE, 2001, pp. 567-573, vol. 4360, Thermosense XXIII.

Alexander Dillenz, Thomas Zweschper and Gerd Busse, "Progress in Ultrasound Phase Thermography", Proceedings of SPIE, 2001, pp. 574-579, vol. 4360, Thermosense XXIII.

* cited by examiner

*Primary Examiner*—Otilia Gabor
*Assistant Examiner*—Christine Sung
(74) *Attorney, Agent, or Firm*—Bachman & LaPointe, P.C.

(57) ABSTRACT

A method of detecting defects in structures, comprising the steps of inducing mechanical energy in a structure via the emission of a broad-band acoustic signal, and capturing over a time interval a plurality of images of the structure each of the plurality of images comprised of a plurality of pixels arranged in a plurality of rows and columns each indicative of an intensity of infrared energy emitted by a portion of the structure.

28 Claims, 4 Drawing Sheets

INFRARED DEFECT DETECTION VIA BROAD-BAND ACOUSTICS

BACKGROUND OF THE INVENTION (1) Field of the Invention

The present invention relates to a method, and apparatus for performing such method, for detecting defects in structures via broad-band acoustic excitation. More specifically, the present invention relates to a method of imparting mechanical energy into a structure via the emission of broad-band acoustic energy and optically recording the subsequent emission of infrared energy from the structure arising from such excitation.

(2) Description of Related Art

It is known in the art of defect detection to induce mechanical nature in a structure via the emission of a single frequency acoustic signal. It is then possible to image or otherwise study the structure to detect infrared emissions arising in the structure as the result of such excitation. Unfortunately, the use of a single frequency substantially limits the ability to inspect the entire structure.

What is therefore needed is an apparatus, and a method of employing the apparatus, to improve defect detection via the emission of single frequency acoustic energy that overcomes the drawbacks of the related art.

SUMMARY OF THE INVENTION

Accordingly, it is an object of the present invention to provide the method of detecting defects in structures which comprises the steps of inducing mechanical energy in a structure via the emission of a broad-band acoustic signal and capturing over a time interval a plurality of images of the structure each of the plurality of images comprised of a plurality of pixels arranged in a plurality of rows and columns each indicative of an intensity of infrared energy emitted by a portion of the structure.

In accordance with the present invention, an apparatus for detecting defects in structures comprises an acoustic frequency generator adapted to generate a broad-band acoustic energy signal, an acoustic energy source adapted to transmit the broad-band acoustic energy signal to the structure, an optical device for detecting and recording as a plurality of images an amount of infrared energy emitted by the structure at a plurality of locations, and an image processor for processing the images.

DETAILED DESCRIPTION OF THE PREFERRED EMBODIMENT(S)

It is a central purpose of the present invention to provide an apparatus and means for using the apparatus to detect defects in parts, in particular machined parts, using infrared detection of mechanical energy induced via broad-band acoustic excitation. In a preferred embodiment, the method of the present invention is applied to the detection of defects in fan blades, compressor blades, and gas turbines, particularly those fabricated from nickel titanium, steel, and titanium alloys. The infrared detection is facilitated by introducing broad-band acoustic energy into the part. The introduced energy causes an increase in temperature in and around the source of structural defects which may be visually detected using infrared imaging equipment. Subsequent images may then be image processed in real time to display an output image. The specifics of how this detection is accomplished is described in greater detail below.

Figure 1:
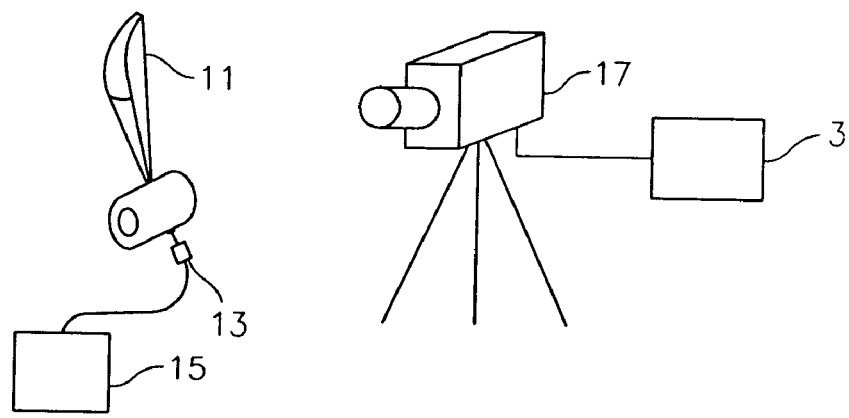
FIG. 1 A diagram of the defect detection system of the present invention.

With reference to FIG. 1, there is illustrated the defect detection system 10 of the present invention. Broad-band mechanical energy is induced in a structure 11 (composite, metal, etc.) with a broad-band acoustic energy source 13 for a short period of time, preferably between 0.1 seconds and 2 seconds, most preferably approximately 1.5 seconds. In a preferred embodiment, the acoustic energy is generated by a acoustic frequency generator 15 in the form of an acoustic energy signal and emitted from a source 13 over a broad spectrum between 1 KHz and 1 MHz. As used herein, "broad-band" refers to a signal comprised of a plurality of frequencies spread out across a spectrum. Preferably, such a spectrum spans a distance of about 1 KHz to about 1 MHz.

Figure 7A:
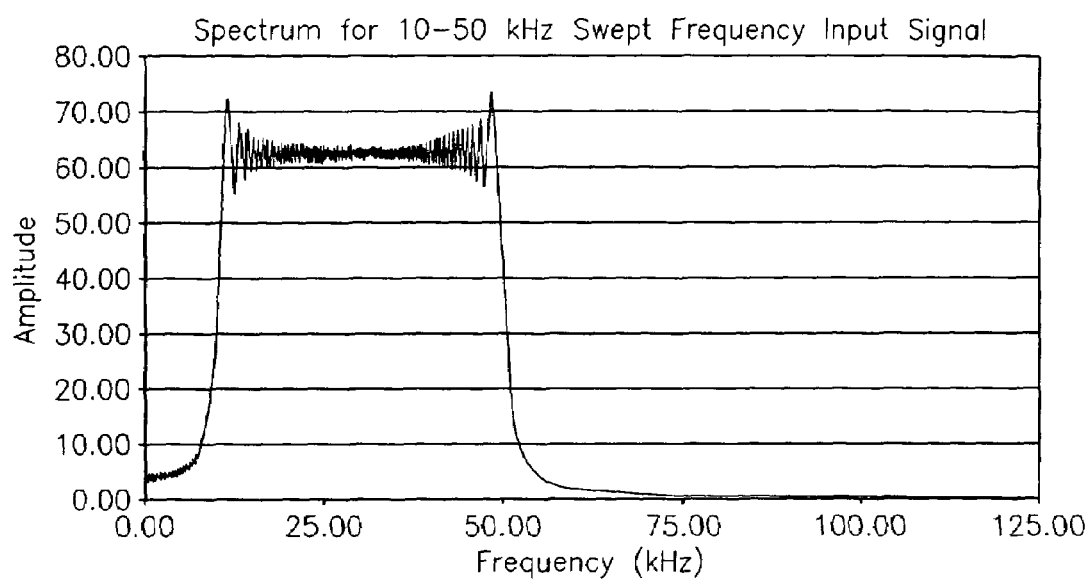
FIG. 7A A graph of a preferred acoustic signal of the present invention in the frequency domain.
Figure 7B:
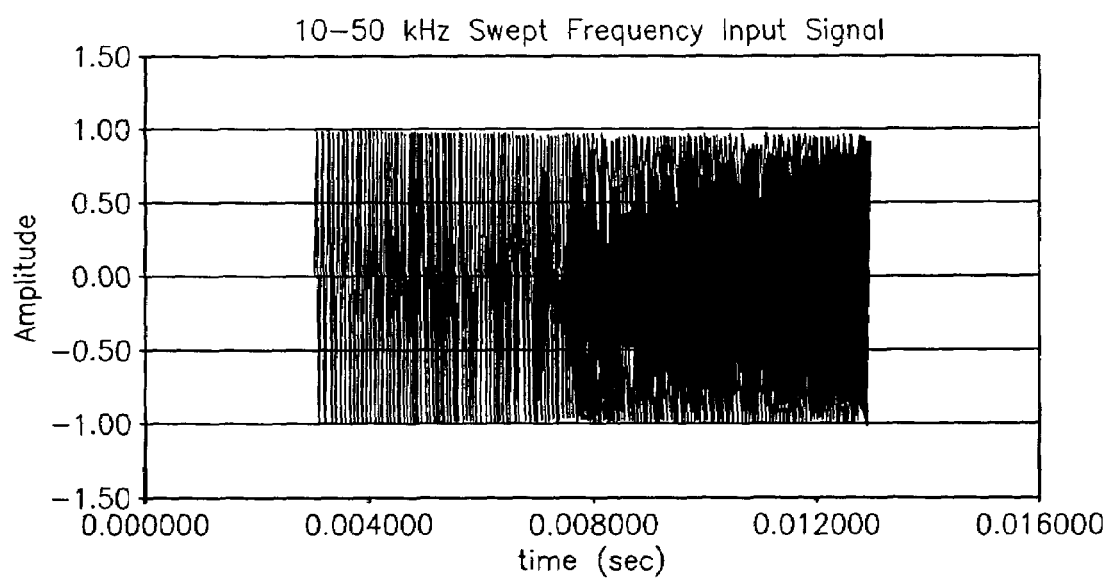
FIG. 7B A graph of a preferred acoustic signal of the present invention in the time domain.

With reference to FIGS. 7A and 7B, there are illustrated frequency and time plots of preferred input acoustic energy profiles. As shown in FIG. 7A the input signal consists, in the frequency domain, of a relatively uniform distribution of frequencies between 10 Khz and 50 Khz. Alternate acoustic energy generators may provide an approximately continuous spectrum energies through the stimulation by an impulse type trigger source. The increased bandwidth of this source may provide an even greater defect detection capability considering complex geometrical component structures such as gas turbine blades and disks.

The acoustic energy produces mechanical vibrations which excite defective features of the structure 11 such as cracks and delaminations. Relative motion of the defective features produce heat causing the emission of infrared energy, which is detected with an optical device 17 and stored as a series of images capable of being stored and processed by image processor 3. In a preferred embodiment, the optical device 17 is an infrared camera and/or fiber optic camera. Preferably, the optical device makes use of a CCD (capacitive-coupled discharge) device. Such devices are particularly sensitive in the infrared range. Excitation of the defective features is dependent upon the location of the defect, the geometry of the structure and the intensity and spectrum of the acoustic energy. Transfer of mechanical energy through the structure has a frequency dependence. To ensure a thorough evaluation for defects, a broad-band energy source is required. Use of a single frequency energy source will limit the inspectability of the whole structure. In addition to the use of broad-band acoustic energy, it is possible to make use of a source 13 which emits at least two non-harmonically related frequencies. As used herein, "non-harmonically related" refers to at least two frequencies which are not integer multiples of the other.

Figure 8A:
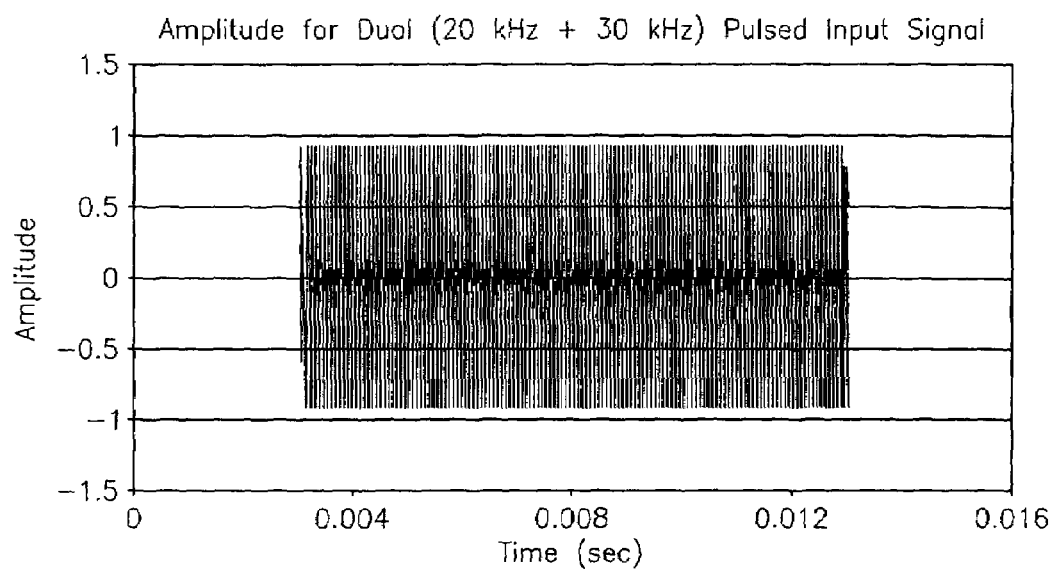
FIG. 8A A graph of two frequency components of a preferred acoustic signal of the present invention in the frequency domain.
Figure 8B:
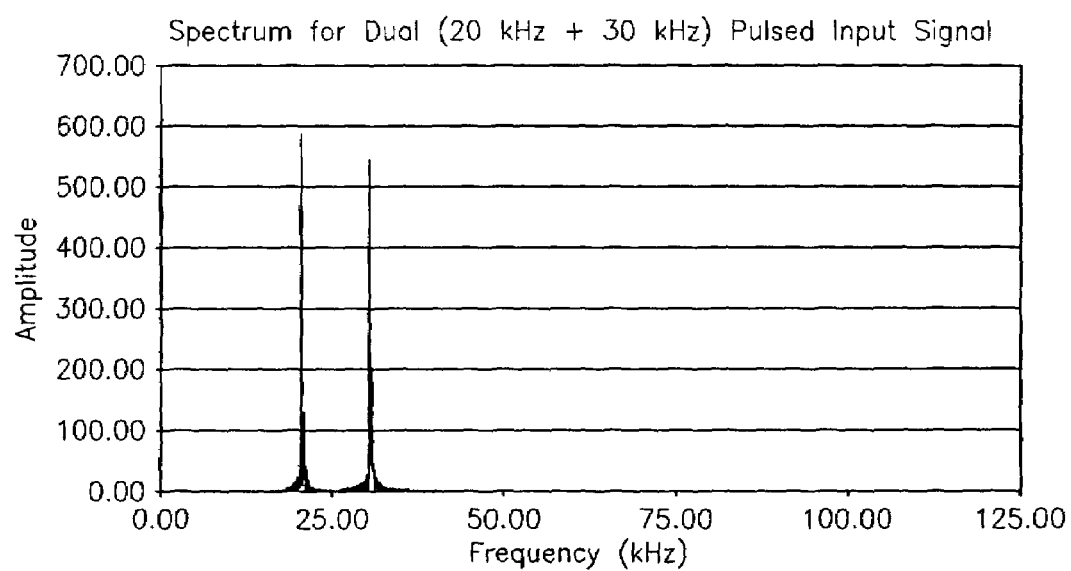
FIG. 8B A graph of two frequency components of a preferred acoustic signal of the present invention in the time domain.

With reference to FIGS. 8A and 8B, there are illustrated frequency and time plots of preferred non-harmonically related frequency input acoustic energy profiles. As shown in FIG. 8B, the input signal consists, in the frequency domain, of a two frequency spikes one centered at 20 Khz and the other centered at 30 Khz. In addition, any number of non-harmonically related frequencies can be utilized.

Figure 2:
FIG. 2 A background image of a structure as recorded by the defect detection system of the present invention.

After introduction of the acoustic energy, real-time imaging processing via image processor 3 is applied to the infrared image data gathered by optical device 17. First, a background image 20 of the structure 11 is acquired prior to introducing the mechanical energy as illustrated with reference to FIG. 2. In a preferred embodiment, the image 20 is comprised of a plurality of pixels arranged in rows in columns. The background image 20 is utilized to remove surface condition variations in subsequent images as described more fully below. Subsequent images are captured by the optical device 17 coincident with and capable of being correlated to each other and with the background image. In a preferred embodiment, a plurality of images is captured at known time intervals. As a result of this imaging method, each corresponding pixel value in each of the series of recorded images represents the intensity of infrared light emitted from a portion of the surface of the structure 11 captured over time.

Figure 3:
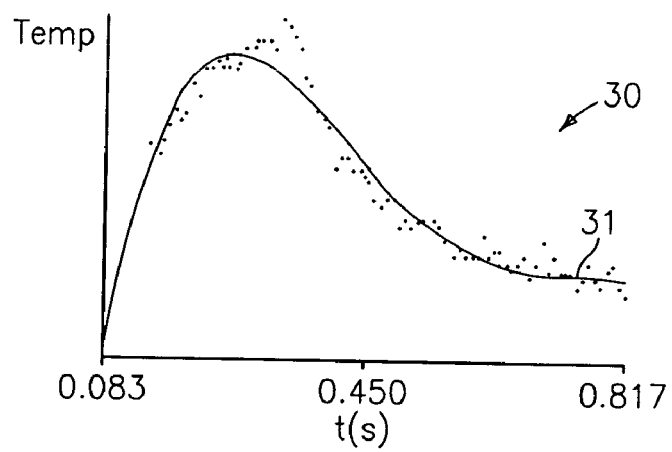
FIG. 3 A graph of recorded pixel values for an exemplary pixel recorded by the defect detection system of the present invention.
Figure 4:
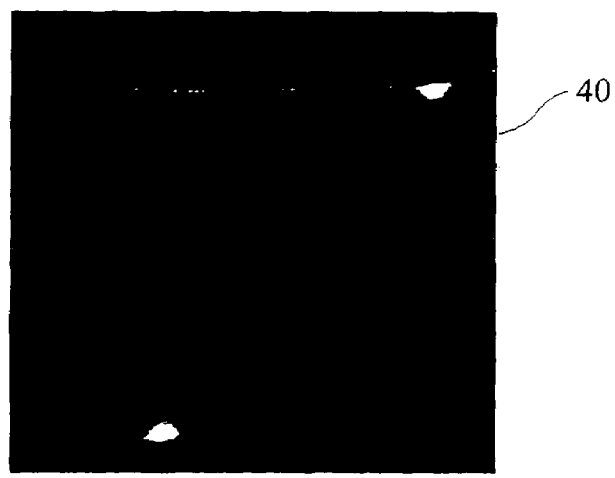
FIG. 4 An exemplary derivative image of a structure as computed in real time by the defect detection system of the present invention.
Figure 5:
FIG. 5 An exemplary derivative image of a structure as computed in real time by the defect detection system of the present invention.

With reference to FIG. 3, there is illustrated a graph 30 of the recorded values for a single exemplary pixel. In the present example, the y-axis intensity value of the pixel has been converted to a temperature reading. In a preferred embodiment, a smooth curve 31 is fitted to the pixel data. By examining such a curve 31, it is possible to compute the maximum heat rate change for each pixel in the image. This process allows for a reduction in input energy and improves the signal to noise ratio. In a preferred embodiment, the pixel values derived from background image 20 are subtracted from each subsequent value so that only changes from the pre-exited structure 11 state are recorded. Once the curve 31 is computed for each pixel subsequent images can be computed from each pixels curve 31. For example, with reference to FIG. 4, there is illustrated an image 40 wherein each pixel is assigned the value of the derivative of temperature change chosen at an appropriate time during excitation. Similarly, with reference to FIG. 5, there is illustrated an image 50 wherein each pixel is assigned the value of the derivative of temperature change chosen at an appropriate time after excitation has ceased. Having computed the curve 31 for each pixel over time, a multitude of images can be generated via image processor 3 and displayed or queried. The most straight forward representation of the pixel data is an image generated to show at any chosen time the magnitude of infrared light emission at each pixel. By computing and observing such images, it is possible to measure the depth at which subsurface defects reside. The further beneath the surface a defect rests, the longer it will take for the mechanical energy arising acoustic excitation of the defect to appear as an infrared emission.

An additional means for the reduction of the input energy requirements is to provide a better coupling mechanism. Specifically, the physical manner in which the source 13 contacts the structure 11 has an effect on the efficiency whereby the acoustic energy is transmitted from the source 13 to the structure 11. The mechanical energy transfer into the structure is quite dependent on the coupling conditions. With structures, other than flat surfaces, the design of the coupling mechanism is therefore important. In a preferred embodiment, custom rigid (i.e., composite, metal) couplers match the structure geometry to the input source. In addition, energy transfer is further optimized when the same or similar material is utilized for the source 13 as for the structure 11. In such an instance, the acoustic impedance of both the source 13 and structure 11 are nearly identical.

Figure 6A:
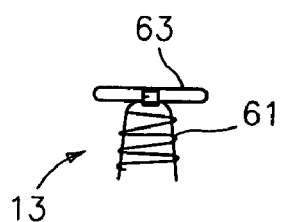
FIG. 6A A diagram of a preferred embodiment of the acoustic source of the present invention.
Figure 6B:
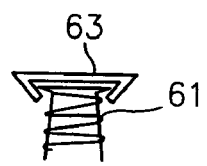
FIG. 6B A diagram of an alternative embodiment of the acoustic source of the present invention.

Another implementation for introducing energy into the structure, is through a floating tip coupling mechanism. This allows for an off-normal positioning of the acoustic source. No additional coupling will be needed in this case. With reference to FIG. 6A, there is illustrated an embodiment of a source 13. Signal carrier 61 receives an acoustic signal from acoustic frequency generator 15 and transmits it to tip 63 in physical contact with signal carrier 61. By placing the tip 63 in contact with a structure 11, the acoustic signal is transmitted to the structure 11. Because the tip 63 is rigidly attached in this embodiment, there exists only one position that maximizes the surface area of contact between the tip 63 and the structure 11. In a preferred embodiment, source 13 comprises a floating tip configuration as illustrated with reference to FIG. 6B. In a floating tip configuration, the tip 63 is not in physical contact with signal carrier 61. As a result, tip 63 is free to pivot or rotate about signal carrier 61. Such a configuration allows greater flexibility in positioning the source 13 in contact with the structure 11 as the tip 63 can pivot to provide a maximum area of contact between the tip 63 and the structure 11.

In addition, alternate acoustic generators, such as an air coupled ultrasonic device or an inductively coupled device, can be employed as the source 13 thus obviating the necessity of establishing physical contact between the source 13 and the structure 11.

It is apparent that there has been provided in accordance with the present invention a method, and apparatus for performing such method, for detecting defects in structures via broad-band acoustic excitation which fully satisfies the objects, means, and advantages set forth previously herein. Specifically, it is contemplated that one could combine any number of techniques disclosed herein, such as parallel beam reception, to further satisfy the object of the present invention. While the present invention has been described in the context of specific embodiments thereof, other alternatives, modifications, and variations will become apparent to those skilled in the art having read the foregoing description. Accordingly, it is intended to embrace those alternatives, modifications, and variations as fall within the broad scope of the appended claims.

What is claimed is:

1. The method of detecting defects in structures, comprising the steps of:

inducing mechanical energy in a structure via the emission of a broad-band acoustic signal;

capturing over a time interval a plurality of images of said structure each of said plurality of images comprised of a plurality of pixels arranged in a plurality of rows and columns each of said pixels indicative of an intensity of infrared energy emitted by a portion of said structure; and computing a curve for each of said plurality of pixels forming said plurality of images whereby each curve is computed from each of said intensities recorded at a single pixel position in said plurality of images at each of said different times.

2. The method of claim 1 wherein said inducing said mechanical energy comprises the steps of:
generating said broad-band acoustic signal; and
introducing said generated acoustic signal to said structure via an acoustic source.

3. The method of claim 2 wherein said introducing said acoustic signal comprises the steps of:
placing said acoustic signal in physical contact with said structure.

4. The method of claim 2 wherein said generating said broad-band acoustic signal comprises the step of generating an acoustic signal having frequencies in the spectrum between 1 KHz and 1 MHz.

5. The method of claim 4 wherein said generating said broad-band acoustic signal comprises the step of generating an acoustic signal comprising a frequency spectrum between 10 KHz and 50 KHz.

6. The method of claim 2 wherein said generating said broad-band acoustic signal comprises generating an acoustic signal comprising at least two non-harmonically related frequencies.

7. The method of claim 6 wherein said generating step comprises generating a signal at a first frequency centered at 20 KHz and at a second frequency centered at 30 KHz.

8. The method of claim 2 wherein said generating said broad-band acoustic signal comprises generating said acoustic signal for a period of time.

9. The method of claim 8 wherein said period of time is between 0.1 and 2 seconds.

10. The method of claim 9 wherein said period of time is approximately 1.5 seconds.

11. The method of claim 2 wherein said capturing said plurality of images comprises the steps of:
capturing a background image of said structure prior to said inducing said mechanical energy; and
capturing at least one additional image each coincident with said background image such that each corresponding pixel in said background image and in each of said at least one additional image possess a value equal to said intensity of infrared light emitted by a portion of said structure at a different time.

12. The method of claim 1 wherein said structure is selected from the group consisting of fan blades, compressor blades, and gas turbine components.

13. The apparatus for detecting defects in structures comprising:
an acoustic frequency generator adapted to generate a broad-band acoustic energy signal;
an acoustic energy source adapted to transmit said broad-band acoustic energy signal to said structure, said acoustic energy source comprises a signal carrier for transmitting said broad-band acoustic energy signal and a tip designed to maximize contact with a structure for receiving said transmitted broad-band acoustic energy signal and transmitting said broad-band acoustic energy signal to said structure;
an optical device for detecting and recording as a plurality of images an amount of infrared energy emitted by said structure at a plurality of locations; and
an image processor for processing said images.

14. The apparatus of claim 13 wherein said tip is in contact with said signal carrier.

15. The apparatus of claim 13 wherein said tip is adapted to pivot about said signal carrier.

16. The apparatus of claim 13 wherein said tip is comprised of a first material substantially similar to a second material from which said structure is formed.

17. The apparatus of claim 16 wherein said first and second material are selected from the group consisting of nickel, nickel alloys, titanium, steel, and titanium alloys.

18. The apparatus of claim 13 wherein said broad-band acoustic energy source is selected from the group consisting of a non-contact and a limited contact source.

19. The apparatus of claim 18 wherein said broad-band acoustic energy source is selected from the group consisting of an air coupled ultrasonic device and an inductively coupled device.

20. The apparatus of claim 13 wherein said optical device is selected from the group consisting of a CCD device and a fiber optic device.

21. The apparatus of claim 13 wherein said broad-band acoustic energy signal spans a spectrum between 1 KHz and 1 MHz.

22. The apparatus of claim 21 wherein said broad-band acoustic energy signal spans a spectrum between 10 KHz and 50 KHz.

23. The apparatus of claim 13 wherein said broad-band acoustic energy signal comprises at least two non-harmonically related frequencies.

24. The apparatus of claim 23 wherein said broad-band acoustic energy signal comprises a first frequency centered at 20 KHz and a second frequency centered at 30 KHz.

25. The apparatus of claim 13 wherein said broad-band acoustic signal has a duration approximating one and a half seconds.

26. The apparatus of claim 13 wherein said structure is selected from the group consisting of fan blades, compressor blades, and gas turbines.

27. The apparatus of claim 13 wherein said tip is adapted to rotate about said signal carrier.

28. The apparatus of claim 13 wherein said tip is shaped to compliment a surface of said structure.

* * * * *

UNITED STATES PATENT AND TRADEMARK OFFICE
CERTIFICATE OF CORRECTION

| | | |
|---|---|---|
| PATENT NO. | : 7,064,330 B2 | Page 1 of 1 |
| APPLICATION NO. | : 10/426399 | |
| DATED | : June 20, 2006 | |
| INVENTOR(S) | : David Raulerson et al. | |

It is certified that error appears in the above-identified patent and that said Letters Patent is hereby corrected as shown below:

In Column 5, claim 11, line 37, "claim 2" should read --claim 1--.

Signed and Sealed this

Twelfth Day of September, 2006

JON W. DUDAS
*Director of the United States Patent and Trademark Office*